United States Patent [19]
Donadello

[11] Patent Number: 5,405,999
[45] Date of Patent: Apr. 11, 1995

[54] PROCESS FOR PREPARING ETHALFLURALIN

[75] Inventor: Graziello Donadello, Valdagno, Italy

[73] Assignee: Finchimica S.p.A., Manerbio, Italy

[21] Appl. No.: 158,261

[22] Filed: Nov. 29, 1993

[30] Foreign Application Priority Data

Sep. 13, 1993 [IT] Italy .................. T093A0667

[51] Int. Cl.$^6$ .................. C07C 209/84; C07C 209/90
[52] U.S. Cl. .................. 564/437; 564/112; 564/406; 564/441
[58] Field of Search .................. 564/112, 406, 437, 441

[56] References Cited

U.S. PATENT DOCUMENTS

| | | | |
|---|---|---|---|
| 4,226,789 | 10/1980 | Eizember et al. | 564/112 |
| 4,638,090 | 1/1987 | Heinrich et al. | 564/437 |
| 4,874,895 | 10/1989 | Graziello | 564/437 |
| 4,970,343 | 11/1990 | Pikarski et al. | 564/437 |
| 5,196,585 | 3/1993 | Wirth | 564/437 |

FOREIGN PATENT DOCUMENTS 0151725  8/1985  European Pat. Off. .

*Primary Examiner*—Richard L. Raymond
*Attorney, Agent, or Firm*—Rothwell, Figg, Ernst & Kurz

[57] ABSTRACT

A process for the preparation of the unsaturated dinitroaniline, ethalfluralin having a level of nitrosamines lower than 0.5 ppm and essentially free from the compound of addition of halogenhydric acid on the methallyl double bond, by treatment with aqueous halogenhydric acid, wherein crude ethalfluralin is treated under agitation with an aqueous solution of hydrobromic acid in the presence of sulfamic acid and a sulfur compound selected from the group consisting of bisulfites, metabisulfites, hydrosulfites, sulfurous acid and gaseous sulfur dioxide.

9 Claims, No Drawings

PROCESS FOR PREPARING ETHALFLURALIN

FIELD OF THE INVENTION

The present invention relates to a process for purifying crude ethalfluralin, which contains trace amounts of nitrosamines, in order to reduce the amount of nitrosamines to a non-dangerous level and particularly to a value lower than 0.5 parts per million (ppm).

BACKGROUND OF THE INVENTION

Ethalfluralin is the commercial name of a herbicide, which is widely used in agriculture and whose chemical name is 4-trifluoromethyl-2,6-dinitro-N-ethyl-N-methallylaniline or (IUPAC) N-ethyl- alpha-alpha-alpha-trifluoro-N-(methylallyl)-2,6-dinitro-p-toluidine.

Ethalfluralin belongs to a wide class of dinitro anilines having herbicidal activity and in such a class is characterized by the presence of an unsaturated methallyl or 2-methyl-2-propenyl group bound to the amino group.

It is known that crude dinitroanilines contain small amounts of nitrosamines, typically from a few ppm to a few hundred ppm. It is assumed that the origin of nitrosamines in dinitroanilines derives from the final stage of the conventional process for preparing dinitroanilines, which consists of reacting the dinitro-chloro-benzene derivative with the desired secondary amine. The dinitro-chloro-benzene derivative may contain small amounts of nitrosating agents, such as nitrogen oxides, which are present as the result of the nitration reaction. The nitrosating agents may react with the amine to form nitrosamines, whose presence in the dinitroanilines is considered undesirable due to the discovery of their carcinogenic properties in animals.

Following the development of highly sensitive methods of analysis, it is possible to ascertain the presence of nitrosamines in dinitroanilines down to a level of 0.02 ppm. The maximum level desired in a commercial product is presently defined at 0.5 ppm.

In order to reduce the amount of nitrosamines, several purification processes have been proposed. Particularly, U.S. Pat. No. 4,226,789 describes a process of treating dinitroanilines with HCl in an aqueous solution, having a concentration of at least 20%, or with gaseous HCl under low pressure. With reference specifically to ethalfluralin, U.S. Pat. No. 4,226,789 teaches the need for using gaseous hydrochloric acid under pressure, since the use of an aqueous solution of hydrochloric acid causes addition reactions to occur across the methallyl double bond resulting in the formation of the chloro derivative and reduction of the titer of ethalfluralin and the overall process yield. Furthermore, the compound produced by the addition of hydrochloric acid to ethalfluralin is stable, and its conversion to ethalfluralin by means of a treatment with sodium hydroxide is not possible.

The treatment with gaseous hydrochloric acid may not be conveniently carried out as an industrial process, since it involves substantial difficulties relating to the availability on the market and preparation of the gaseous hydrochloric acid as well as a substantial increase in the plant investment costs.

U.S. Pat. No. 4,874,895 describes a process for purifying trifluralin (4-trifluoromethyl-2,6-dinitro-N,N-di-n-propylaniline) by using aqueous hydrobromic acid in the presence of additives consisting of sulfamic acid and bisulfite. The disclosed process is advantageous since it is adapted not only for the removal of the nitrosamines, but also to avoid the growth of nitrosamines in the purified trifluralin. Moreover, the process allows the almost quantitative recovery of the treatment solution and its recycling for several purification cycles.

As compared with the several trifluralin purification processes described in literature wherein the processes are generally applicable to the whole class of the dinitroanilines, the process disclosed in U.S. Pat. No. 4,874,895 is strictly limited to trifluralin. Furthermore, in view of the teaching provided by U.S. Pat. No. 4,226,789, the treatment with aqueous halogenhydric acids was not considered as industrially applicable for the purification of unsaturated dinitroanilines.

SUMMARY OF THE INVENTION

Surprisingly, it has been found that aqueous hydrobromic acid, under the process conditions adopted for removing nitrosamines from ethalfluralin, has a behavior that is not analogous to that of hydrochloric acid, since it is not susceptible to causing the formation of addition products across the double bond present in ethalfluralin. In view of such a discovery, the present invention is a process for the purification of the unsaturated dinitroaniline, crude ethalfluralin, by treating the ethalfluralin with aqueous halogenhydric acid, suitable to reduce the level of nitrosamine contained in the ethalfluralin to a value lower than 0.5 ppm, while avoiding the formation of compounds caused by the addition of the halogenhydric acid on the unsaturated bond. The crude ethalfluralin is treated with an aqueous solution of hydrobromic acid in the presence of sulfamic acid and a sulfur compound selected from the group consisting of bisulfites, metabisulfites, hydrosulfites, sulfurous acid and gaseous sulfur dioxide.

DETAILED DESCRIPTION OF THE INVENTION

The process of the invention allows the amount of nitrosamines to be reduced to the desired level, without reducing the titer of ethalfluralin.

Typically, the treatment with the aqueous hydrobromic acid solution is carried out at a temperature from 20° C. to 90° C., preferably from 60° C. to 80° C., for a time period from 10 minutes to 4 hours.

The hydrobromic acid concentration in the aqueous solution is typically between 15% and 50% by weight, preferably between 23% and 27% by weight. The latter concentration range is preferred because of the more favorable kinetics, the greater ease of separation between the aqueous phase and the ethalfluralin phase at the end of the treatment. The latter concentration range also is preferred because of the possibility of using again the solution for several recyclings which, when exhausted, may eventually be regenerated by distillation. The distillation of an aqueous solution of hydrobromic acid having a concentration from 23% to 27% by weight leads to an azeotropic mixture having a concentration of hydrobromic acid of 48% by weight which may be easily reused in the process after dilution by the optional addition of fresh hydrobromic acid.

The ratio between the aqueous solution of hydrobromic acid and ethalfluralin is typically from 0.2 to 0.8 l of aqueous acidic solution per kg of ethalfluralin, and preferably from 0.3 to 0.5 l/kg.

The amount of sulfamic acid used is typically from 0.1 to 3 g/l of the hydrobromic acid solution, and preferably from 0.4 to 0.7 g/l. Sulfamic acid is preferably added as an aqueous solution having a concentration from 10% to 20% by weight which allows a simple dosage to achieve the above-mentioned concentration of sulfamic acid in the hydrobromic acid solution.

The sulfur compound is selected from bisulfites, metabisulfites, hydrosulfites, preferably of alkali metals, particularly of sodium sulfurous acid and gaseous sulfur dioxide. The sulfur compound is added in an amount corresponding with a sulfur dioxide content of from 0.3 to 1.2 g/l of the aqueous hydrobromic acid solution.

Sodium bisulfite is preferred, since it may be used in commercially available forms, such as anhydrous sodium bisulfite. The sodium bisulfite has a content of $SO_2$ of about 60% by weight, or as a solution of sodium bisulfite has a content of $SO_2$ from 24% to 26% by weight, or as sodium metabisulfite has a content of $SO_2$ of about 65% by weight.

According to the process of the invention, crude ethalfluralin is mixed under strong agitation with the aqueous hydrobromic acid solution to which sulfamic acid and the sulfur compound have been added. The molten organic phase is then separated from the aqueous hydrobromic acid solution. The refined ethalfluralin is recovered from the molten organic phase by washing—while still hot—with an alkaline water solution to neutralize the pH. The molten mass is then solidified by cooling.

The aqueous phase of hydrobromic acid separated from the molten organic phase is then treated again with sulfamic acid and a sulfur compound at a temperature higher than about 50° C. The aqueous phase may then be reused for the treatment of a new batch of ethalfluralin. The aqueous solution may be recycled up to twenty times, without reducing its effectiveness in reducing the level of nitrosamines to a value below 0.5 ppm and without an addition reaction occurring on the double bond. The exhausted hydrobromic acid solution may then be regenerated by distillation.

The ethalfluralin obtained is extremely resistant to the formation of nitrosamines during the thermal treatment to which it is subjected for the preparation of herbicidal compositions.

EXAMPLE 1

Preparation of Ethalfluralin 960 g water and 810 g 4-chloro-3,5-dinitrobenzotrifluoride are introduced into a glass balloon having a volume of 3000 ml. The glass balloon is placed in a thermostatic bath and is provided with a stirrer, reflux condenser, thermometer and charging funnel.

297 g N-ethylmethallylamine are added, dropwise under strong stirring while maintaining the temperature below 40° C.

After the N-ethylmethallylamine is added, the temperature of the reaction mixture is maintained at 35°–40° C. for 20 minutes. 405 g of a 30% sodium hydroxide aqueous solution are then added, while maintaining the temperature at 40°–45° C. After the sodium hydroxide is added, the reaction mixture is heated to 60° C. and then to 70° C. in about 1 hour. This temperature is maintained for 30 minutes.

405 g water are then added, while maintaining the temperature at 70° C. After the water has been added, the reaction mixture is maintained at 70° C. for 30 minutes, while the pH is adjusted to 6.5 by adding 7 g of 36% HCl The stirrer is stopped, and the reaction mixture is allowed to clear at 60°–70° C. The two phases are then separated. The lower phase consists of ethalfluralin and weighs 1000 g.

The gas chromatographic analysis showed a titer higher than 95% as well as the absence of the product of addition across the double bond.

The GC/TEA analysis showed a nitrosamine content of 47 ppm.

EXAMPLE 2

Removal of nitrosamines contained in Ethalfluralin with 36% hydrochloric acid 25 g of an aqueous solution of 36% HCl are added to 200 g of ethalfluralin containing 47 ppm of nitrosamines in a glass balloon provided with a stirrer. The solution is heated at 70° C. under stirring for 1 hour.

The stirrer is stopped and the two layers are allowed to separate. The organic layer is poured dropwise into a glass balloon containing 50 ml water and a 5 ml aqueous solution of 10% $Na_2CO_3$. The temperature is maintained at 60°–70° C. under stirring, and the pH, which must be higher than 7, is controlled. Stirring is maintained for 15 minutes, and the reaction mixture is allowed to clear.

The organic phase is separated and analyzed. The nitrosamine content by GC/TEA analysis is lower than 0.2 ppm. The gas chromatographic analysis of the product shows that the content of the product of addition across the double bond is 2.0%.

In a second test carried out according to the same procedure as above, but with the use of 50 g of 36% HCl and for a time of 2 hours, a product is obtained having a nitrosamine content that cannot be determined by GC/TEA analysis (the sensitivity threshold of the instrument is 0.05 ppm). However, the content of the product of the addition across the double bond is higher than 5%,

EXAMPLE 3

Nitrosamine removal with 25% hydrobromic acid 600 g of crude ethalfluralin containing 47 ppm of nitrosamines are mixed in a glass balloon, provided with stirrer and reflux condenser, with 200 g of an aqueous solution of 25% HBr, 0.1 g sulfamic acid and 0.1 ml of a 30% sodium bisulfite aqueous solution.

The reaction mixture is heated to 80° C. under stirring and maintained at that temperature for 3 hours. The stirrer is stopped, and the reaction mixture is allowed to clear. The organic layer is first separated, then poured dropwise into a glass balloon containing 200 ml water and 10 ml of a 10% aqueous solution of $Na_2CO_3$, after which it is stirred at 60°–70° C. for 15 minutes. The stirrer is stopped, and the two phases are allowed to separate.

The organic layer is analyzed and shows by GC/TEA analysis a nitrosamine content lower than 0.2 ppm (sensitivity threshold: 0.05 ppm). The gas chromatographic analysis shows a titer higher than 95% as well as the absence of the product of addition across the double bond.

What is claimed is:

1. A process for the preparation of the unsaturated dinitroaniline, ethalfluralin, having a level of nitrosamines lower than 0.5 ppm and essentially free from the compound of addition of halogenhydric acid on the methallyl double bond, by treatment with aqueous halogenhydric acid, comprising the steps of:

treating crude ethalfluralin under agitation with an aqueous solution of hydrobromic acid in the presence of sulfamic acid and a sulfur compound selected from the group consisting of bisulfites, metabisulfites, hydrosulfites, sulfurous acid and gaseous sulfur dioxide; and separating the ethalfluralin from the aqueous hydrobromic acid solution.

2. A process according to claim 1, wherein the aqueous hydrobromic acid solution has a concentration from 15% to 50% by weight.

3. A process according to claim 2, wherein the aqueous hydrobromic acid solution has a concentration from 23% to 27% by weight.

4. A process according to claim 1, wherein the ratio between the aqueous hydrobromic acid solution and crude ethalfluralin is from 0.2 to 0.8 l/kg.

5. A process according to claim 4, wherein the ratio between the aqueous hydrobromic acid solution and crude ethalfluralin is from 0.4 to 0.6 l/kg.

6. A process according to claim 1, wherein the amount of sulfamic acid added to the hydrobromic acid solution is from 0.1 to 3 g/l 7. A process according to claim 6, wherein the amount of sulfamic acid added to the hydrobromic acid solution is from 0.4 to 0.7 g/l 8. A process according to claim 1, wherein the amount of the sulfur compound added to the hydrobromic acid solution corresponds to a content of sulfur dioxide from 0.3 to 1.2 g/l 9. A process according to claim 8, wherein the amount of the sulfur compound added to the hydrobromic acid solution corresponds to a content of sulfur dioxide from 0.5 to 0.8 g/l.

* * * * *